United States Patent [19]

Piclin et al.

[11] Patent Number: 5,549,562

[45] Date of Patent: Aug. 27, 1996

[54] SELF-CONTAINED DRIP APPARATUS

[75] Inventors: Jean-Jacques Piclin, Viterne; Gilbert Thibaut, Nancy; Michel Boisson, Saint-Andre, all of France

[73] Assignee: A.D.E.C.E.F., Viterne, France

[21] Appl. No.: 190,019

[22] PCT Filed: Oct. 13, 1992

[86] PCT No.: PCT/FR92/00960

§ 371 Date: Sep. 29, 1994

§ 102(e) Date: Sep. 29, 1994

[87] PCT Pub. No.: WO94/08645

PCT Pub. Date: Apr. 28, 1994

[51] Int. Cl.$^6$ .................................. A61M 5/142
[52] U.S. Cl. .................................. 604/134
[58] Field of Search .................... 604/141, 134, 604/131

[56] References Cited

U.S. PATENT DOCUMENTS

| | | | |
|---|---|---|---|
| 3,565,292 | 2/1971 | Jinotti | 604/134 |
| 3,734,351 | 5/1973 | Gaudin | 604/134 |
| 3,895,741 | 7/1975 | Nugent | 604/141 |
| 4,157,771 | 6/1979 | Smith | 222/103 |
| 4,504,267 | 3/1985 | Parmelee et al. | 604/134 |
| 4,557,728 | 12/1985 | Sealfon et al. | 604/134 |
| 5,328,477 | 7/1994 | Sitko | 604/134 |

FOREIGN PATENT DOCUMENTS

| | | |
|---|---|---|
| 289361 | 11/1988 | European Pat. Off. . |
| 1107676 | 1/1956 | France . |
| 2561923 | 10/1985 | France . |
| 2570949 | 4/1986 | France . |
| 2677887 | 12/1992 | France . |
| 4129271 | 9/1992 | Germany . |

*Primary Examiner*—Paul J. Hirsch
*Attorney, Agent, or Firm*—Weiser & Associates, P.C.

[57] ABSTRACT

An apparatus for the infusion of a liquid contained in an infusion bag. The apparatus includes a plate for receiving an infusion bag, and a box having a closable lid. Interaction between the lid, the plate and an elastic spring mechanism located inside the box results in the expulsion of fluid from the infusion bag. The elastic spring mechanism includes four arms that articulate in pairs to form two cross structures that are biased together with springs. Respective ends of the two cross structures are connected by rollers, while opposing ends of the two cross structures are connected to inside portions of the box.

1 Claim, 1 Drawing Sheet

5,549,562

SELF-CONTAINED DRIP APPARATUS

BACKGROUND OF THE INVENTION

The subject of the present invention is an autonomous apparatus for injecting a patient by infusion of a liquid contained in an infusion bag, the device including means for expelling the liquid from the said bag and for injecting it into the patient.

An application will be described hereinbelow for human infusion. It will be understood that the device of the invention may also find an application in the veterinary field.

The problem posed consists of injecting a patient, in general but without limitation at the scene of a road accident or other casuality, with a liquid by infusion. In general, the liquid is a biological liquid making it possible to compensate for the various water losses of the patient (for example a state of shock).

Conventionally, the liquid is contained in an infusion bag suspended from a bracket, or held by hand at least temporarily by the personnel administering treatment, from which it flows simply by the effect of gravity.

Although this configuration is perfectly functional in a hospital environment, the same is not true during emergency assistance, especially outdoors, for example at the time of road or other accidents.

To this end, a certain number of autonomous infusion devices have already been proposed, directly joined to a limb of the patient (arm or leg) or suspended therefrom by some means (belt clip, etc.).

None of tile known devices is entirely satisfactory.

Thus, in document FR-2,561,923, a device of this type is proposed, in which the infusion liquid is expelled from a bag by a piston actuated by a spring.

This device has the drawback of resorting to non-standard infusion bags and of exerting on the bag a pressure (force) which is not constant and which does not permit an even flow rate of the infusion liquid.

Similarly, document FR-2,570,949 describes a device of the same type for a standard infusion bag, in which the liquid is expelled by compressed air pressure. The bag is arranged in a leaktight chamber. It has not yet been possible to use these devices suitably, because of problems of leaktightness and regulation of the flow rate of the gas pressure.

Such devices furthermore require a pressure reducer and are therefore relatively expensive.

SUMMARY OF THE INVENTION

It is the object of the present invention to overcome these various drawbacks of the devices of the prior art, by allowing:

the use of standard infusion bags in sterile flexible packaging;

the fastening of the apparatus on the thigh or the forearm of the patient; and operating under the following conditions:

handling by one person;

autonomous operation after fitting;

adjustable infusion time for a standard dose;

low cost price;

maintenance cost during storage as low as possible;

light weight;

absolute reliability;

constant flow rate from when the bag is full until it is completely empty.

The objectives obtained with an autonomous apparatus for injecting a patient by infusion of a liquid contained in an infusion bag, the device including means for expelling the liquid from the bag and for injecting it into the patient, wherein the expulsion means includes a plate on which the infusion bag is arranged, the plate being arranged in a box fitted with a lid which can be folded down onto the plate. The plate is pressed by an elastic means primed by closing the lid and which tends to push the plate back toward the lid so as to expel the liquid from the infusion bag.

BRIEF DESCRIPTION OF THE DRAWINGS

The invention will be better understood with the aid of the description given hereinbelow of one embodiment, given by way of non-limiting example, with reference to the attached drawings, in which.

DETAILED DESCRIPTION OF THE INVENTION

Figure 1:
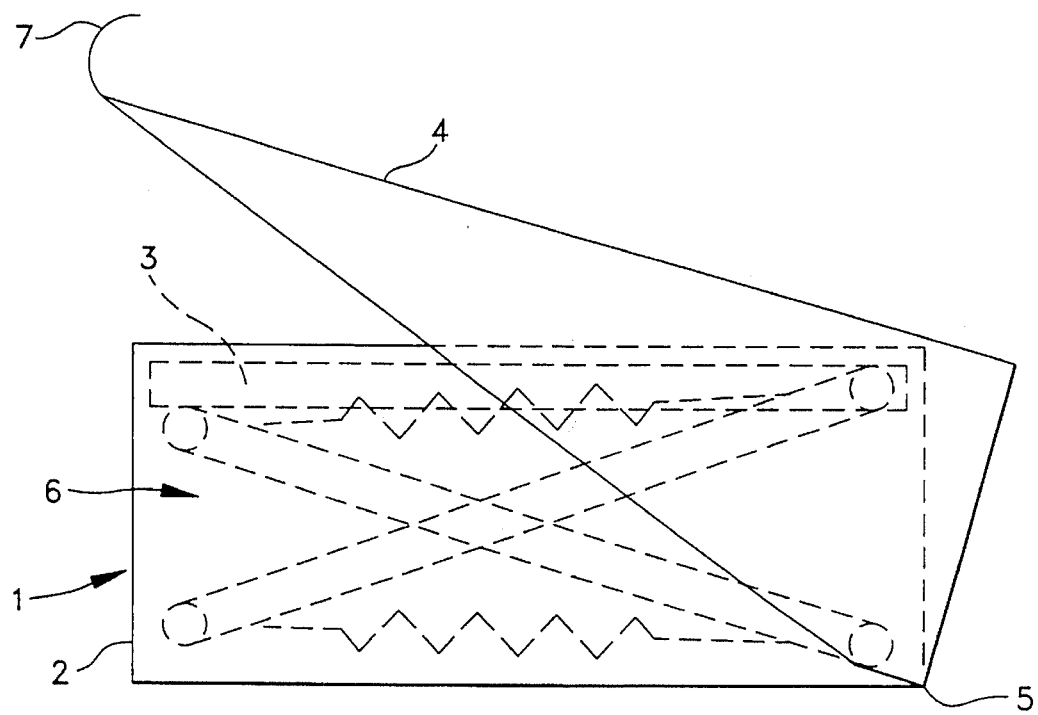
FIG. 1 is a view of the device of the invention in side elevation, with the lid open.

The infusion device, generally labelled (1), essentially comprises:

a box (2);

a mobile plate (3), a lid (4) articulated on the box (2) at (5), an expulsion mechanism (6).

The elements linked with the injection of the product have not been represented.

In operation, the infusion bag is arranged on the plate and the lid (4) is closed using the handle (7). This simple movement primes the mechanism (6) which, by virtue of the elastic means, tends to push the plate back (upward) in order to expel the liquid to be infused from the bag (which is sandwiched between the plate and the lid).

Figure 2:
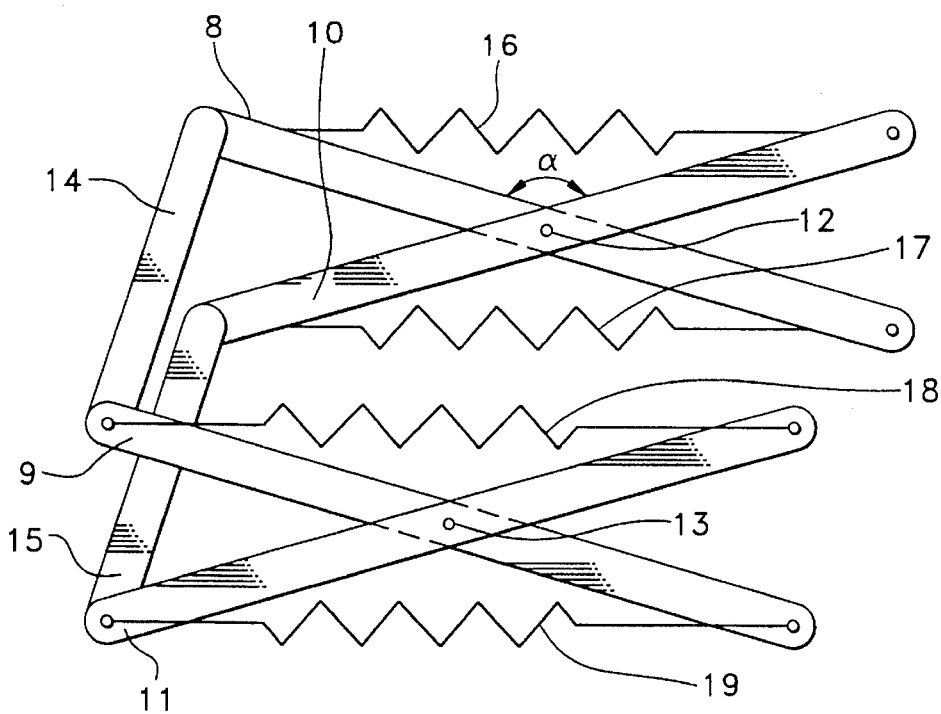
FIG. 2 is a perspective view of the elastic pressing means of the plate.

The mechanism (6) will now be described with reference to FIG. 2.

The mechanism is composed of four arms (8, 9, 10, 11) articulated in pairs at their middle (at 12, 13) to form two crosses.

Each cross is symmetrically connected to the other by rotatable rollers (14, 15) arranged respectively at the ends of the arms (8, 9) and (10, 11).

The other ends of the arms are connected, in the case of (8) and (9), to the box (2), and in the case of (10) and (11), to the plate (3).

The arms of each cross are connected by two springs (16, 17) and (18, 19) respectively, arranged on each side of the articulations (12, 13).

The angle between the two arms of each cross will be called $\alpha$. By symmetry, it will be noted that the angle $\alpha$ has the same value for both crosses.

Operation is as follows.

When the small bag is full on the mobile plate and the lid is folded down, the mobile plate descends, tensioning the springs and increasing the angle $\alpha$. When the mobile plate rises back up, the holder bag empties, and the force in the springs decreases, as does as the angle $\alpha$.

By expediently defining the force in the springs, the original angle and the angle at end of travel of the mobile plate and the length of the arms, the resultant force applied on the mobile plate makes it possible to obtain constant pressure in the small bag and therefore a constant flow rate.

This device may also find an application in other, non-medical fields, for example in the food field, or the injection of water into plants for watering them.

We claim:

1. An apparatus for infusing a patient with a liquid contained in an infusion bag, comprising:

means for expelling the liquid from the bag, for injection into the patient, including a plate for receiving the infusion bag and a box fitted with a lid, wherein the plate is arranged in the box so that the lid is foldable over the infusion bag and the plate; and elastic means for pressing on the plate responsive to closure of the lid so that pressure between the plate and the lid expels liquid from the infusion bag, wherein the elastic means includes;

first and second cross members, each cross member including a first arm and a second arm, and each arm having a first end, a second end, and a middle portion, wherein the first arm and the second arm are connected at their middle portions;

first and second spring members, wherein the first spring member is connected between the first end of the first arm and the second end of the second arm, and the second spring member is connected between the first end of the second arm and the second end of the first arm; and first and second rotatable rollers, wherein the first rotatable roller is connected between the first end of the first arm of the first cross member and the first end of the first arm of the second cross member, and the second rotatable roller is connected between the first end of the second arm of the first cross member and the first end of the second arm of the second cross member;

wherein the second ends of the first arms of the first and second cross members are attached to inside portions of the box, and the second ends of the second arms of the first and second cross members are attached to the plate, wherein the elastic means and the plate cooperate to define a resilient platform such that closure of the lid causes contact between the lid and the infusion bag received on the plate, and wherein the plate is pushed toward the lid by the elastic means, for expelling the liquid from the infusion bag.

* * * * *